(12) United States Patent
Iimori et al.

(10) Patent No.: US 6,379,948 B1
(45) Date of Patent: Apr. 30, 2002

(54) MICROBE SKB-1152 STRAIN, AND METHOD OF BLEACHING PULP THEREWITH

(75) Inventors: Takeshi Iimori; Reiji Kaneko; Hiroshi Yoshikawa; Makoto Machida, all of Yamaguchi (JP)

(73) Assignee: Nippon Seishi Kabushiki Kaisha (JP)

( * ) Notice: Subject to any disclaimer, the term of this patent is extended or adjusted under 35 U.S.C. 154(b) by 0 days.

(21) Appl. No.: 08/406,883

(22) PCT Filed: Jul. 28, 1994

(86) PCT No.: PCT/JP94/01245

§ 371 Date: May 22, 1998

§ 102(e) Date: May 22, 1995

(87) PCT Pub. No.: WO95/04131

PCT Pub. Date: Feb. 9, 1995

(30) Foreign Application Priority Data

Jul. 28, 1993 (JP) .............................................. 5-207322
May 16, 1994 (JP) .............................................. 6-126919

(51) Int. Cl.⁷ ................................................. C12N 1/14
(52) U.S. Cl. .................................... 435/254.1; 435/278
(58) Field of Search ............................... 435/278, 254.1; 162/72

(56) References Cited

U.S. PATENT DOCUMENTS

| | | | | |
|---|---|---|---|---|
| 3,617,436 A | * | 11/1971 | Assarssan et al. ............ | 162/72 |
| 4,830,708 A | * | 5/1989 | Paice et al. ................... | 162/72 |
| 5,055,159 A | * | 10/1991 | Blanchette ................... | 162/72 |
| 5,149,648 A | * | 9/1992 | Nishida et al. .............. | 435/192 |
| 5,427,945 A | * | 6/1995 | Blanchette et al. ......... | 435/278 |
| 5,431,820 A | * | 7/1995 | Nishida et al. ............. | 210/611 |
| 5,434,071 A | * | 7/1995 | Rosenberg et al. ......... | 435/200 |
| 5,437,992 A | * | 8/1995 | Bodie et al. ................ | 435/200 |
| 5,460,697 A | * | 10/1995 | Akhtar et al. ................. | 162/72 |
| 5,476,789 A | * | 12/1995 | Farrell et al. ................ | 435/267 |

OTHER PUBLICATIONS

Moreira et al., Bioresource Technology, 70 (1999) pp. 255–260.*

* cited by examiner

Primary Examiner—Curtis E. Sherrer
(74) Attorney, Agent, or Firm—Millen, White, Zelano & Branigan, P.C.

(57) ABSTRACT

Pulp bleaching method using SKB-1152 strain which is a lignin-degrading strain having high lignin degrading activity and pulp bleaching activity, or the culture produced using the SKB-1152. When the SKB-1152 strain of this invention or the culture produced using the same is to bleach pulp, the same bio-bleaching method as in the prior report may be used and there is no need for any special culture conditions. The SKB-1152 strain of the invention can be collected from decolorized areas formed in a culture rue medium which contains, lignin and/or pulp containing residual lignin, and being inoculated with a isolating source sample and cultured.

10 Claims, No Drawings

MICROBE SKB-1152 STRAIN, AND METHOD OF BLEACHING PULP THEREWITH

FIELD OF THE INVENTION

This invention relates to a novel strain, and to a pulp bleaching method using the same. In particular, it relates to a novel lignin-degrading strain having high lignin degrading activity and pulp bleaching activity, and to a pulp bleaching method using the same.

BACKGROUND OF THE INVENTION

Conventionally, in the bleaching of wood pulp, chlorine and chlorine compounds were widely used to remove residual lignin in the pulp.

In recent years, however, it has become clear that these chlorine compounds generate dioxin, which is a toxic substance, and hence it is now necessary to limit their use as a matter of urgency.

Various bleaching methods have been proposed to replace chlorine compounds, and one such effective technique, "bio-bleaching" that makes use of strains or their enzymes, is now attracting considerable attention.

In the past, many attempts have been made to degrade the lignin in wood using strains for use in the paper pulp industry, etc.

A series of Basidiomycetes known as white rotted fungi that selectively degrade lignin were used for this purpose.

Coriolus versicolor and Phanerocheate chrysporium are typical examples of such fungi with lignin. degrading activity, and they have also been used in research and development.

However, these strain of fungi do not have sufficient lignin degrading activity, and they were therefore inadequate for improving the brightness of pulp. Moreover, their selectivity is low so that in addition to lignin, they degrade polysaccharides such as cellulose and hemicellulose at the same time. This leads to poorer pulp quality and lower pulp yields, hence it was so far impossible to use these fungi industrially.

The inventors studied methods of isolating and screening novel strain that had excellent pulp bleaching activity, and could be used industrially. They were thus able to develop such a method for novel strain that can identify and isolate lignin-degrading strain with high accuracy (Tokugan Hei 5-85731).

Based on the aforesaid selection method for lignin-degrading strain, the inventors carried out detailed studies, using rotted wood or fruiting body as a isolating source, in order to isolate novel strain having a high pulp bleaching activity, As a result, they succeeded in isolating a novel strain that not only has high lignin-degrading activity, but which is also capable of greatly improving the brightness of pulp, and thereby arrived at the present invention.

It is therefore a first object of this invention to provide a lignin-degrading strain for pulp bleaching that has both high lignin-degrading activity, and thermophilic pulp bleaching activity.

It is a second object of this invention to provide a pulp bleaching method that can be used industrially, employing this novel strain having high lignin-degrading activity and/or a culture prepared from the strain.

DISCLOSURE OF THE INVENTION

The aforesaid objects of the invention are achieved by the strain SKB-1152 that has high lignin-degrading activity and thermophilic pulp bleaching activity, and by a pulp bleaching method using this strain.

This invention will now be described in more detail. The novel strain SKB-1152 of this invention has the following microbiological characteristics:

(1) Growth in Culture Medium

| Type of culture medium | Growth |
| --- | --- |
| Malt extract agar medium | +++ |
| Potato extract dextrose medium | +++ |
| Czapeck agar medium | +++ |
| Sabouraud agar medium | +++ |
| Synthetic mucor agar medium | +++ |
| YpSs agar medium | +++ |
| Culture conditions: 30° C., 3 days | +++ |
| Growth: Slight +/Medium ++/Vigorous +++ | +++ |

(2) Physiological and Ecological Characteristics

The pH required for growth (Potato extract dextrose medium, 30° C., 3 days culture) is in the range 3–9.

The strain will not grow at pH 2 or lower, or at pH 10 or higher. The optimum pH range is 4–8.

The temperature required for growth (Potato extract dextrose agar medium, pH 5.6, 4 days culture) lies in the range 20–40° C. The strain will not grow at 50° C. or higher.

The optimum temperature range is 28–37° C.

The phenoloxidase reaction (30° C., 3 day culture) gives a slight or negative reaction.

The colonies (Potato extract dextrose agar medium, pH 5.6, 4 day culture) resemble thin white felt.

Physiological and ecological characteristics, and mycological characteristics such as growth on various culture media, were examined in detail, however this strain could not be identified with any known strain.

As will be clear from the examples described hereinafter, this strain has better lignin-degrading activity and pulp bleaching activity than Coriolus versicolor and Phanerocheate chrysporium which have conventionally been regarded as typical lignin-degrading strain.

No conventionally known strain has both excellent lignin-degrading and pulp bleaching activity. The inventors therefore identified this fungi as a new strain, gave it the name SKB-1152, and deposited a sample to the National Institute of Bioscience and Human-Technology, Agency of Industrial Science & Technology, Ministry of International Trade and Industry (Contribution No. FERM P-4718).

As there are still some unresolved questions regarding the classification of this strain of fungi, a precise identification is difficult to make at this time and the results of future research must be awaited.

An outline of how SKB-1152 is isolated and selected will now be given.

According to this method, a culture medium containing lignin or pulp with residual lignin, is inoculated with a isolating source sample of rotted wood or fruiting body, and strain having lignin-degrading activity are isolated depending on the formation or non-formation of a decolorized area in the medium.

The lignin used herein may be Kraft lignin or sulfate lignin, and the pulp with residual lignin may be a chemical pulp such as Kraft pulp. The medium used for the culture may be a liquid medium wherein a culture solution is merely added to pulp, or a solid culture wherein pulp is solidified with agar or the like.

The preparation of the medium for the aforesaid isolation and selection method, and the selection of lignin-degrading strain, may be carried out according to methods known in the report.

This method of isolating and selecting lignin-degrading strain is simpler and more precise than the conventional method of phenoloxidase detection, and it also has an advantage in that lignin-degrading strain can be isolated and selected from rotted wood or fruiting body.

Next, the pulp bleaching method using the novel strain SKB-1152 of this invention will be described.

In the pulp bleaching method according to this invention, pulp is basically treated with SKB-1152 or a culture produced using this strain, and the strain is then cultured for a predetermined time. There is no particular limitation on the culture conditions provided that they are within the range of physiological characteristics of the aforesaid strain.

Herein, what is meant by a culture produced using SKB-1152 is a mixture of microbes and culture solution that has been obtained by culture of this strain. In the context of the invention, this includes not only microbes isolated from a microbial culture, but also the residues remaining after the microbe is isolated, and the culture solution remaining after all solid matter has been eliminated from the culture.

The pulp used in this invention may be a chemical pulp or mechanical pulp, there being no particular limitation on the type of pulp provided that it contains residual lignin. Moreover, there is no limitation on the form of the pulp used for the culture provided that strain grow easily on it and it is easy to bleach.

The pulp concentration, temperature and pH used for the culture may be chosen suitably within a range wherein the strain has physiological activity.

However, from the viewpoint of airation and growth of the strain, in the case of a static clture, the pulp concentration is preferably within the range 15–60%, while in the case of a shaking culture, it is preferably not higher than 15% and more preferably not higher than 10%.

As the pH in the culture varies as the strain grows, the pH reaches a value convenient for producing the strain naturally. It is consequently unnecessary to adjust the pH precisely, and provided it is within the range 3–10, there is no effect on pulp bleaching activity. The culture temperature is preferably within the range 25–40° C., particularly good results being obtained when the temperature is in the region of 37° C.

Also, to decrease the time required to bleach the pulp, various nutrients may be added if necessary.

An outstanding feature of this invention is that when the SKB-1152 of this invention is used to bleach pulp as described hereinabove, the same bio-bleaching method as in the prior report be used, and there is no need for any special culture conditions.

The reaction mechanism whereby the strain SKB-1152 of this invention bleaches pulp is unclear at the present time, however it may be supposed that as this strain also has high lignin-degrading activity, the bleaching action is similar to lignin degradation.

Conventionally, lignin degradation is thought to be an oxidative degradation, hence it may be conjectured that the bleaching reaction of the SKB-1152 of this invention is also an oxidative degradation reaction.

As will be clear from the bleaching performance confirmed by means of examples described hereinafter, the strain of this invention also has high lignin-degrading activity. In addition to pulp bleaching, the strain of this invention has various industrial uses in wood industries requiring lignin removal, for example decoloration pulp effluent, and lignin degradation or breaking up of lignin into smaller molecules. In these cases also, a culture containing the lignin raw material that it is desired to treat may be inoculated with the strain of this invention, and the strain then cultured for a predetermined time.

PREFERRED EMBODIMENTS OF THE INVENTION

This invention will now be described with reference to specific examples, but it should be understood that the invention is not to be construed as being limited by these examples in any way.

First, samples of rotted wood or fruiting body collected from forests all over Japan were surface sterilized by flame, and used to inoculate commercial unbleached pulp agar culture. Of the strain which grew on the culture medium, those which formed decolorized areas were isolated. These strain were then used to bleach commercial oxygen-bleached pulp at a pulp concentration of 20% at 30° C. for 7 days, and the brightness after bleaching was measured. SKB-1152 was selected as the strain which increased brightness the most.

EXAMPLE 1

A potato dextrose broth medium containing 0.4% potato extract and 2% glucose (DIFCO Co,) was inoculated with SKB-1152, and incubated statically for 1 week. The mycelial mat was homogenized in a whirling blender, the mycelial suspension added to commercial oxygen-bleached pulp which had been heat-sterilized at 120° C. for 15 min such that the final pulp concentration was 20%, and it was incubated statically to stand at 30° C. and 37° C. for 7 days.

500 ml water was then added, the pulp was defiberized in a mixer and a handmade paper sheet prepared. The brightness of the sheet was measured with a Hunter-type reflectometer (JIS P8123), and its kappa number was measured (JIS 8211-1976). As a comparison, the same procedure was performed for Coriolus versicolor and Phanerocheate chrysporium, which are typical lignin-degrading strains. The results are shown in Table 1.

TABLE 1

| Strain | Brightness | Kappa number |
| --- | --- | --- |
| Untreated | 51.5 | 11.2 |
| Coriolus versicolor | 57.6 | 9.7 |
| *Phanerocheate chrysporium* (30° C.) | 67.2 | 7.3 |
| (37° C.) | 70.1 | 6.9 |
| SKB-1152 (30° C.) | 79.3 | 4.5 |
| (37° C.) | 79.9 | 4.1 |

As can be seen from Table 1, the strain SKB-1152 according to this invention has far superior bleaching activity to that of conventional strain, and it was found in particular that a great increase of brightness and reduction of kappa number are obtained at high temperature.

EXAMPLE 2

The three strains used in Example 1 were cultured in a potato extract dextrose agar medium. A disk of each microbe culture cut out with a cork borer was then used to inoculate a plate prepared by adding 4 ml water to 1 g of a wood powder of Eucalyptus globulus sterilized under high pressure.

After incubation for 2 weeks at 30° C. for Coriolus versicolor and at 37° C. for the other two strains, the amounts of Klasson lignin (JIS P8008-1961) and acid-soluble lignin ("Chemistry of Lignin" edited by Junzo Nakano, Unipress, p.53) in the cultured wood powder were measured. The results are shown in Table 2,

TABLE 2

| Strain | Klasson lignin(%) | Acid soluble lignin(%) | Total lignin(%) | Lignin loss (%) |
|---|---|---|---|---|
| Untreated* | 23.79 | 3.60 | 27.39 | — |
| Coriolus versicolor | 22.74 | 3.67 | 26.41 | 3.6 |
| Phanerocheate chrysporium | 23.17 | 3.70 | 26.87 | 1.9 |
| SKB-1152 | 17.32 | 3.52 | 20.84 | 23.9 |

*) Water was added to wood powder, the mixture sterilized at high pressure and left for 2 weeks As can be seen from Table 2, the strain SKB-1152 of this invention has a far superior lignin-degrading activity than conventionally known strains such as Coriolus versicolor.

EXAMPLE 3

Bleaching was performed by three strains according to the same method as that of Example 1, excepting that unbleached pulp was used instead of oxygen-bleached pulp, and incubated for 3 days or 7 days. A handmade paper sheet was also prepared as in Example 1, and the brightness was measured. The results are shown in Table 3.

TABLE 3

| Strain | Brightness | |
|---|---|---|
|  | 3 days | 7 days |
| Untreated |  | 28.7 |
| Coriolus versicolor (30° C.) | 32.4 | 36.8 |
| Phanerocheate chrysporium (37° C.) | 30.3 | 42.1 |
| SKB-1152 (37° C.) | 39.2 | 58.4 |

As shown in Table 3, the strain SKB-1152 of this invention also has a far superior bleaching activity on unbleached pulp than conventional strains.

EXAMPLE 4

A mycelial suspension of SKB-1152 was prepared as in Example 1, and a fixed amount of this mycelial suspension was added to commercial oxygen-bleached pulp so that the final pulp concentrations were 25%, 33.3%, 50% and 66.6%. These cultures were incubated at 37° C. for 3 days or 7 days. After incubation, a handmade paper sheet was prepared according to the same method as that of Example 1, and the brightness of the sheet was measured. The results are shown in Table 4.

TABLE 4

| Pulp concentration | Brightness | |
|---|---|---|
|  | 3 day culture | 7 day culture |
| 25% | 68.0 | 78.4 |
| 33.3% | 66.5 | 78.2 |
| 50.0% | 62.2 | 76.5 |
| 66.6% | 64.0 | 75.5 |

As shown in Table 4, the strain SKB-1152 of this invention has a good pulp bleaching activity even at high pulp concentration.

EXAMPLE 5

A mycelial suspension of SKB-1152 was prepared as in Example 1, and a fixed amount of this mycelial suspension was added to commercial oxygen-bleached pulp so that the final pulp concentrations were 2%, 1% and 0.5%. After culturing each sample at 37° C. in a rotating shaker at a 140 rpm, the samples were cultured for 1 day or 2 days, a handmade paper sheet was prepared according to the same method as that of Example 1, and the brightness of the sheet was measured. The results are shown in Table 5.

TABLE 5

| Pulp concentration | Brightness | |
|---|---|---|
|  | 1 day culture | 2 day culture |
| 2% | 59.1 | 69.5 |
| 1% | 60.3 | 69.8 |
| 0.5% | 61.0 | 69.9 |

*Untreated pulp 47.9%

As shown in Table 5, the strain SKB-1152 of this invention has a good pulp bleaching activity even at low pulp concentration.

EXAMPLE 6 oxygen-bleached pulp was bleached by SKB-1152 according to the method of Example 1, the initial pH being adjusted in steps of 1 from 2 to 11. After microbial bleaching, incubated at 37° C. for 3 days or 7 days, a handmade paper sheet prepared as in Example 1, and the brightness of the sheet measured. The results are shown in Table 6.

TABLE 6

| Initial pH (%) | 2 | 3 | 4 | 5 | 6 | 7 | 8 |
|---|---|---|---|---|---|---|---|
| Whiteness on 3rd day | 52.3 | 74.2 | 74.3 | 74.1 | 73.8 | 73.7 | 74.1 |
| Whiteness on 7th day | 52.4 | 79.3 | 79.6 | 79.9 | 79.7 | 79.5 | 79.3 |
| Initial pH (%) | 9 | 10 | 11 | | | | |
| Whiteness on 3rd day | 74.0 | 73.4 | 68.7 | | | | |
| Whiteness on 7th day | 79.0 | 79.7 | 79.4 | | | | |

As shown in Table 6, the initial pH in pulp bleaching by SKB-1152 of this invention has no effect on pulp bleaching activity provided that it lies within the range 3–10.

EXAMPLE 7

Oxygen-bleached pulp was bleached by SKB-1152 according to the method of Example 1, the culture temperature being adjusted respectively to 25° C., 30° C., 33° C., 37° C., 40° C. and 43° C. After incubation of 7 days, a handmade paper sheet was prepared as in Example 1, and the brightness was measured. The results are shown in Table 7.

TABLE 7

| Culture temperature(° C.) | 25 | 30 | 33 | 37 | 40 | 43 |
|---|---|---|---|---|---|---|
| Brightness (%) | 73.7 | 77.8 | 79.2 | 79.8 | 76.8 | 55.6 |

As shown in Table 7, the temperature at which pulp bleaching is performed by SKB-1152 of this invention is preferably 25–40° C., the most satisfactory results being obtained in the vicinity of 37° C.

EXAMPLE 8

Bleaching of commercial oxygen-bleached pulp was performed by SKB-1152 by the same method as that of Example 1 (37° C., 7 days), and a microbially treated pulp of brightness 80.1% was obtained. This was bleached with hydrogen peroxide under the following conditions to obtain a pulp of brightness 85.8%.
(Hydrogen Peroxide Bleaching Conditions)
NaOH/pulp=1.5%, pulp concentration=10%, $H_2O_2$/pulp=0.5%, 60° C., 120 min.

This pulp was treated at 105° C. for 18 hours, the brightness after treatment was measured, and the color restoration due to heating was evaluated. As a comparison, a commercial oxygen-bleached pulp bleached to a brightness of 85.6% with chlorine dioxide was treated in the same way, and the color restoration due to heating evaluated. The results are shown in Table 8.

TABLE 8

|  | Before heat treatment Brightness(%) | After heat treatment Brightness(%) | PC value |
| --- | --- | --- | --- |
| Microbe-$H_2O_2$ bleaching | 85.8 | 83.1 | 0.54 |
| Chlorine dioxide bleaching | 85.6 | 82.1 | 0.74 |

The results of Table 8 show that restoration of color due to heating is less with the pulp bleached by microbes and hydrogen peroxide, than with the pulp bleached by chlorine dioxide.

Field of Application

The lignin-decomposing strain of this invention has a far superior lignin-degrading activity and pulp bleaching performance than conventionally known strains. It therefore promises to provide a pulp bleaching method in paper manufacturing processes which does not use chlorine-type chemicals.

What is claimed is:

1. A strain SKB-1152 (FERM BP.4718) having high lignin-degrading activity and thermophilic pulp bleaching activity.

2. A pulp bleaching method characterized in that pulp is treated by the strain SKB-1152 defined in claim 1.

3. A pulp bleaching method characterized in that pulp is treated by a culture produced using said strain SKB-1152 defined in claim 1.

4. A pulp bleaching method as defined in claim 3 which comprises the step of producing said culture in a solid culture medium having a pulp concentration of 15–60%.

5. A pulp bleaching method as defined in claim 3 which comprises the step of producing said culture by shaking and employing a solid culture medium having a pulp concentration which does not exceed 15%.

6. A pulp bleaching method as defined in claim 3 wherein a treatment temperature is 25–40° C.

7. A pulp bleaching method as defined in claim 2 wherein a treatment temperature is 25–40° C.

8. A pulp bleaching method as defined in claim 7 wherein a treatment temperature is 37° C.

9. A pulp bleaching method which comprises bleaching said pulp by the strain SKB-1152 defined in claim 1, and treating the bleached pulp with alkali.

10. A pulp bleaching method which comprises bleaching pulp with a culture produced by the strain SKB-1152 defined in claim 1, and treating the bleached pulp with alkali.

* * * * *

UNITED STATES PATENT AND TRADEMARK OFFICE
CERTIFICATE OF CORRECTION

PATENT NO.    : 6,379,948 B1
DATED         : April 30, 2002
INVENTOR(S)   : Iimori et al.

It is certified that error appears in the above-identified patent and that said Letters Patent is hereby corrected as shown below:

<u>Title page, Item [54] and Column 1, lines 1and 2,</u>
Please delete the title in its entirety and insert the correct title as follows:

-- MICROBE SKB-1152 STRAIN, METHOD OF SEPARATING THE SAME, AND METHOD OF BLEACHING PULP THEREWITH --.

Item [57], ABSTRACT,
Line 5, after "is" insert -- used --;
Line 9, delete "rue".

Signed and Sealed this

Twenty-second Day of April, 2003

JAMES E. ROGAN
*Director of the United States Patent and Trademark Office*